United States Patent [19]

Konno et al.

[11] Patent Number: 5,385,900
[45] Date of Patent: Jan. 31, 1995

[54] QUINOLINE CARBOXYLIC ACID DERIVATIVES

[75] Inventors: Fujiko Konno, Chiba; Akihiro Shibata, Yachiyo; Hideaki Matsuda, Abiko; Takemitsu Asaoka, Narita; Ryuichi Kawahara, Ichikawa; Naokata Taido, Funabashi; Tadayuki Kuraishi, Chiba; Sunao Takeda, Ichihara, all of Japan

[73] Assignee: SS Pharmaceutical Co., Ltd., Tokyo, Japan

[21] Appl. No.: 149,134

[22] Filed: Nov. 8, 1993

Related U.S. Application Data

[63] Continuation of Ser. No. 842,191, filed as PCT/JP91/00954, Jul. 17, 1991, abandoned.

[30] Foreign Application Priority Data

Jul. 19, 1990 [JP] Japan ..................... 191339
Apr. 12, 1991 [JP] Japan ..................... 79774

[51] Int. Cl.⁶ ..................... A61K 31/55; C07D 243/08
[52] U.S. Cl. ..................... 514/218; 540/492; 540/544; 540/575; 540/597
[58] Field of Search ................ 514/218; 540/492, 544, 540/575, 597

[56] References Cited

U.S. PATENT DOCUMENTS 4,945,160 7/1990 Kiely et al. .................... 540/481
5,140,033 8/1992 Schriewer et al. ............... 514/312

FOREIGN PATENT DOCUMENTS 60-214777 10/1985 Japan .
61-1682 1/1986 Japan .
63-132885 6/1988 Japan .
63-196580 8/1988 Japan .
2115181 4/1990 Japan .

OTHER PUBLICATIONS

Ito et al., Chemical Abstract, 110(5), 39031a, 1988.
Ito et al. Chemical Abstract, 109(15),129070W, 1988.
Journal of Medicinal Chemistry, vol. 33, 1990, pp.142–146, C. B. Ziegler, Jr. et al., "Synthesis and Structure-Activity Relationships of New 7[3-(-Fluoromethyl)Piperazinyl]-and -(-Fluorohomopiperazinyl) Quinoline Antibacterials".
Journal of Medicinal Chemistry, vol. 28, 1985, pp. 1558–1564, D. T. W. Chu, et al., "Synthesis and Structure-Activity Relationships of Novel Arylfluoroquinolone Antibacterial Agents".

*Primary Examiner*—Mukund J. Shah
*Assistant Examiner*—Y. N. Gupta
*Attorney, Agent, or Firm*—Oblon, Spivak, McClelland, Maier & Neustadt

[57] ABSTRACT

A quinolone carboxylic acid derivative having the following formula (1),

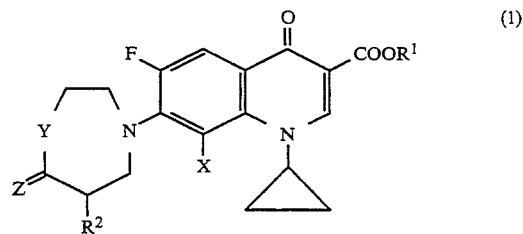

wherein $R^1$ is a hydrogen atom, an alkyl group, an aralkyl group, an ester residual group which can be hydrolyzed in living bodies, $R^2$ is a hydrogen atom or an amino group which may be substituted by one or two lower alkyl groups, X is a hydrogen atom or a halogen atom, Y is $CH_2$, O, S, SO, $SO_2$, or $N-R^3$, wherein $R^3$ is a hydrogen atom or a lower alkyl group, and Z is an oxygen atom or two hydrogen atoms; or a salt thereof; and an antimicrobial agent comprising the same. The compound exhibits a superior antimicrobial activity, especially against gram positive microorganisms, and is thus useful for the treatments and prevention of various infectious diseases in clinics.

24 Claims, No Drawings

QUINOLINE CARBOXYLIC ACID DERIVATIVES

This application is a continuation of application Ser. No. 07/842,191, filed as PCT/JP91/00954, Jul. 17, 1991, now abandoned.

TECHNICAL FIELD

The present invention relates to a novel quinolone carboxylic acid derivative and a salt thereof which exhibit excellent antimicrobial activity against both Gram positive and Gram negative microorganisms.

BACKGROUND ART

Synthetic antimicrobial agents such as nalidixic acid, piromidic acid, and the like are known as drugs for curing infectious diseases caused by Gram negative microorganisms. They exhibit, however, only deficient effects on intractable diseases such as pseudomoniasis and the like.

On the other hand, quinolone carboxylic acid derivatives substituted with a fluorine atom at 6 position, such as norfloxacin, ofloxacin, and cyprofloxacin, or quinolone carboxylic acid derivatives substituted with a chlorine atom at 8 position have been developed (Japanese Patent Laid-open (ko-kai) Nos. 225181/1986, 90183/1989) and clinically used because of their strong antimicrobial activity.

These conventional synthetic antimicrobial agents had defects of insufficient absorptivity in a living body, providing only low bioavailability, and of a low antimicrobial activity against Gram positive microorganisms.

Therefore, development of antimicrobial agents having strong antimicrobial activity against both Gram positive and Gram negative microorganisms, including resistant bacteria, and superior absorptivity in living bodies has been desired.

In view of such a situation, the present inventors have synthesized a number of quinolone derivatives and studied their antimicrobial activity and absorptivity in a living body, and found that quinolone carboxylic acid derivatives of the following formula (1) and their salts exhibited antimicrobial activities against Gram positive microorganisms much stronger than conventional quinolone carboxylic acid derivatives, while maintaining their strong antimicrobial activities against Gram negative microorganisms, as well as excellent absorptivity. Such findings have led to the completion of the present invention.

DISCLOSURE OF THE INVENTION

The present invention provides a quinolone carboxylic acid derivative having the following formula (1),

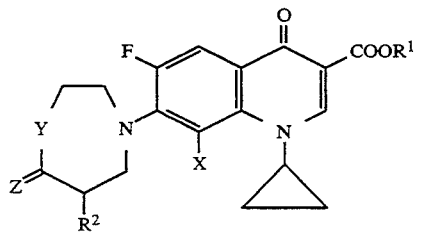
(1)

wherein $R^1$ is a hydrogen atom, an alkyl group, an aralkyl group, or an ester residual group which can be hydrolyzed in living bodies, $R^2$ is a hydrogen atom or an amino group which may be substituted by one or two lower alkyl groups, X is a hydrogen atom or a halogen atom, Y is $CH_2$, O, S, SO, $SO_2$, or $N-R^3$, wherein $R^3$ is a hydrogen atom or a lower alkyl group, and Z is an oxygen atom or two hydrogen atoms; or a salt thereof.

The present invention also provides an antimicrobial agent comprising a quinolone carboxylic acid derivative of formula (1) or a salt thereof as an effective component.

BEST MODE FOR CARRYING OUT THE INVENTION

Given as examples of groups represented by $R^1$ in formula (1) are, as alkyl groups, linear or branched alkyl groups having 1–12 carbon atoms, e.g., methyl, ethyl, n-propyl, i-propyl, n-butyl, i-butyl, t-butyl, n-pentyl, n-hexyl, and the like; as aralkyl groups, benzyl, phenyl ethyl, methyl benzyl, naphtyl methyl, and the like; and as ester residual groups which can be hydrolyzed in living bodies, alkanoyloxyalkyl, alkoxycarbonyloxyalkyl, carbamoylalkyl, alkoxyalkyl, and the like; specifically, acetoxymethyl, 1-acetoxyethyl, ethoxycarbonyloxymethyl, carbamoylmethyl, carbamoylethyl, methoxymethyl, methoxyethyl, and the like. Examples of amino groups which may be substituted by one or two lower alkyl groups, represented by $R^2$, include amino, methylamino, ethylamino, isopropylamino, dimethylamino, diethylamino, diisopropylamino, and the like. Examples given of halogen atoms represented by X are chlorine, fluorine, bromine, iodine, and the like. Lower alkyl groups used in the present invention may be linear or branched alkyl groups having 1–5 carbon atoms, e.g., methyl, ethyl, i-propyl, sec-butyl, t-butyl, amyl, and the like.

When $R^2$ in formula (1) is other than hydrogen, the carbon atom to which $R^2$ is bonded is asymmetrical, so that there are optical isomers; R and S compounds, for compounds (1) of the present invention. The present invention includes both the optical isomers and the racemate.

As examples of the salts of the compounds of formula (1) of the present invention, salts of alkali metal, inorganic acid, organic acid, and the like are given, and more specifically, lithium salts, sodium salts, potassium salts, and the like, as salts of alkali metal; hydrochloride, sulfate, nitrate, hydrobromide, phosphate, and the like, as salts of inorganic acids; and acetate, fumarate, maleate, lactate, citrate, tartarate, malate, oxalate, methanesulfonate, benzenesulfonate, p-toluenesulfonate, and the like, as salts of organic acid.

In the preparation of the compound of formula (1) of the present invention [Compounds (1a) and (1b)] Compound (2) and Compound (3), for example, are reacted according to the following reaction scheme to produce Compound (1a), and Compound (1a) is halogenated to produce Compound (1b).

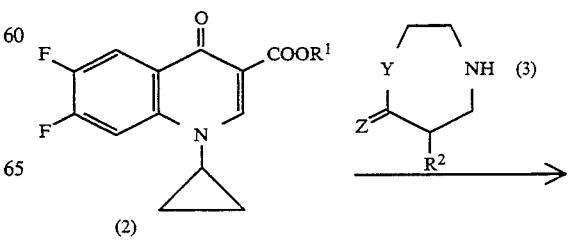

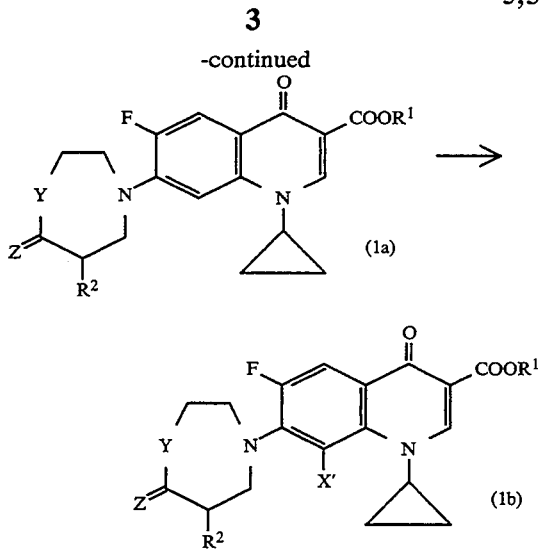

wherein X' is a halogen atom, and $R^1$, $R^2$, Y and Z are the same as those previously defined.

The raw material, Compound (2), is a known compound and can be prepared by the method described, for example, in Journal of Medicinal Chemistry, 31, 983 (1989). Compound (3) is also a known compound and can be prepared by the method described, for example, in Journal of American Chemical Society, 106, 630 (1984).

In order to prepare Compound (1a) from Compound (2) and Compound (3), 1 mol of Compound (2) is reacted with 1-5 mols of Compound (3) in a solvent such as acetonitrile, dimethylsulfoxide, or the like at room temperature to 100° C. for 1-7 days. After the reaction, precipitate is collected by filtration and washed with a suitable solvent, e.g., methanol, chloroform, ether, etc., to obtain a crude product. The crude product is purified by silica gel column chromatography or by recrystallization to obtain Compound (1a).

The preparation of Compound (1b) from Compound (1a) can be carried out by a method described, for example, in Japanese Patent Laid-open 90183/1989; that is, 1 mol of Compound (1a) is reacted with 1-10 mols of a halogenizing agent, such as sulfuryl chloride, chlorine, bromine, iodine, N-chlorosuccinic acid imide, N-bromosuccinic acid imide, or the like, in a suitable solvent, such as chloroform, dichloromethane, acetic acid, methanol, ethanol, or the like, at 0°-100° C. for 1-48 hours. After the reaction, water is added to collect precipitate by filtration and the precipitate is washed with water to produce a crude product. This crude product is purified by silica gel column chromatography or by the recrystallization to obtain Compound (1b).

If necessary, Compound (1) thus obtained is converted into a salt, such as a salt of alkali metal, inorganic acid, organic acid, or the like, according to a conventional method.

When Compound (1) of this invention thus prepared is used as an antimicrobial agent, it is administered orally at a dose of 200 to 800 mg per day or parenterally at a dose of 5 to 40 mg per day, depending on the weight, the age, the sex, the physical conditions, or the symptom of the patient or the manner of administration.

Compound (1) can be formed into various antimicrobial preparations, such as tablets, granules, powders, capsules, suspensions, injections, suppositories, or the like, according to conventional methods. When solid preparations are produced, compound (1) is mixed with excipients, and as required, with binders, disintegrators, lubricants, coloring agents, sweetening agents, flavoring agents, fillers, coating agents, sugar-coating agents, and the like, and formed into preparations such as tablets, granules, powders, capsules, suppositories, or the like according to known methods. When compound (1) is made into a preparation for injection, it is dissolved, suspended, or emulsified into an aqueous medium such as distilled water, or made into powder which is dissolvable when it is injected. Intravenous, intraarterial, intraportal, intraperitoneal, intramuscular, or subcutaneous injection are applicable.

EXAMPLES

The present invention is hereinafter described in more detail by way of examples and test examples, which are not intended to be limiting thereof.

EXAMPLE 1

1-Cyclopropyl-6-fluoro-7-(2,3,4,5,6,7-hexahydro-1H-1,4-diazepin-5-one-1-yl)-4-oxoquinoline-3-carboxylic acid (Compound No. 1)

0,265 g of 1-cyclopropyl-6,7-difluoro-4-oxoquinoline-3-carboxylic acid and 0.200 g of 2,3,4,5,6,7-hexahydro-1H-1,4-diazepin-5-one dissolved into 20 ml of acetonitrile and refluxed for 3 days. After cooling, the precipitate was collected by filtration, washed with chloroform, methanol, and ether in this order to obtain 0.300 g of colorless crystals of the target compound (yield: 83%).

$IR\nu_{max}^{KBr}$ cm$^{-1}$: 1720, 1660 1620 $^1$H-NHR δ ppm(NaOD+D$_2$O): 0.76-1.48(m, 4H), 2.50-3.80(m, 9H), 7.10(d, J=7.7 Hz, 1H), 7.56(d, J=14.1 Hz, 1H), 8.48(s, 1H) m.p.: 300° C. or above

EXAMPLE 2

8-Chloro-1-cyclopropyl-6-fluoro-7-(2,3,4,5,6,7-hexahydro-1H-1,4-diazepin-5-one-1-yl)-4-oxoquinoline-3-carboxylic acid (Compound No. 2)

0.84 ml of sulfuryl chloride was added dropwise to a suspension of 1.50 g of 1-cyclopropyl-6-fluoro-7-(2,3,4,5,6,7-hexahydro-1H-1,4-diazepin-5-one-1-yl)-4-oxoquinoline-3-carboxylic acid in 30 ml of chloroform, and the mixture was stirred for 12 hours at room temperature. After an addition of ice water, the precipitate was collected by filtration, washed with water, dried in air, and recrystallized in ethanol-chloroform to obtain 0.87 g pale yellow crystals of the target compound (yield: 53.0%).

$IR\nu_{max}^{KBr}$ cm$^{-1}$: 1720, 1660 1620 $^1$H-NHR δ (CD$_3$OD+CDCl$_3$): 0.80-1.50(m, 4H), 2.50-3.00(m, 2H), 3.30-3.64(m, 7H), 7.52(s, 1H), 8.10(d, J=11.6 Hz, 1H), 9.02(s, 1H) m.p.: 282°-284° C. (decomposed)

EXAMPLES 3-9

Compound Nos. 3-9 listed in Table 1 were prepared in the same manner as in Example 1. Physicochemical data of these compounds are given in Table 2.

TABLE 1

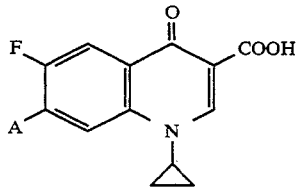

| Compound No. | A | Compound No. | A |
|---|---|---|---|
| 3 | CH₃-N(C=O)-CH₂CH₂-N— (3-methyl-2-oxo-1,4-diazepan-1-yl) | 7 | HN-piperazinyl with NH₂ substituent |
| 4 | hexahydroazepinyl with NH₂ | 8 | (R)-hexahydroazepinyl with NH₂ |
| 5 | hexahydroazepinyl | 9 | (S)-hexahydroazepinyl with NH₂ |
| 6 | hexahydroazepinyl with N(CH₃)₂ | | |

TABLE 2

| Compound No. | Melting Point(°C.) | Property | IR (KBr, cm$^{-1}$) | $^1$H-NMR ($\delta$ ppm) |
|---|---|---|---|---|
| 3 | 268–271 (decomposed) | light yellow powder | 1720, 1650, 1625 | 1.10–1,60(m, 4H), 2.80–3.15(m, 5H), 3.40–3.85(m, 7H), 7.44(d, J=7.7Hz, 1H), 7.98(d, J=14.1Hz, 1H), 8.76(s, 1H). (CDCl₃+CD₃OD). |
| 4 | 205–209 | colorless powder | 1630 | 1.00–2.20(m, 10H), 3.00–4.00(m, 6H), 7.28(d, J=(.0Hz, 1H), 7.96(d, J=15.4Hz, 1H), 8.76(s, 1H). (CDCl₃+CD₃OD). |
| 5 | 228–230.5 | light yellow powder | 1720, 1620 | 1.10–1.40(m, 4H), 1.40–2.10(m, 8H), 3.05–3.30(m, 1H), 3.30–3.80(m, 4H), 7.18(d, J=9.0Hz, 1H), 7.90(d, J=15.4Hz, 1H), 8.70(s. 1H). (CDCl₃). |
| 6 | 184–187 | light yellow powder | 1720, 1625 | 1.00–1.65(m, 4H), 1.65–2.20(m, 6H), 2.32(s, 6H), 2.68–3.05(m, 1H), 3.10–3.75(m, 4H), 3.75–4.05(m, 1H), 7.25(d, J=9.6Hz, 1H), 7.90(d, J−15.4Hz, 1HO, 8.68(s, 1H). (CDCl₃). |
| 7 | 199–203 (decomposed) | light brown powder | 1720. 1610 | 1.00–1.40(m, 4H), 2.50–3.10(m, 4H), 3.10–4.00(m, 10H), 7.39(d, J=7.9Hz, 1H), 7.71(d, J=15.2Hz. 1H), 8.54(s, 1H), (DMSO-d₆). |
| 8 | 215–217 | colorless powder | 1625 | 1.00–2.20(m, 10H), 3.00–4.00(m, 6H), 7.28(d, J=7.7Hz, 1H), 7.96(d, J=15.4Hz, 1H), 8.75(s, 1H). (CDCl₃+CD₃OD). |
| 9 | 218–221 | colorless powder | 1725, 1620 | 1.00–2.20(m, 10H), 2.60–4.00(m, 6H), 7.25(d, J=7.7Hz, 1H), 7.85(d, J=15.4Hz, 1H), 8.75(s, 1H). (CDCl₃+CD₃OD). |

EXAMPLES 10–16

Reactions were carried out in the same manner as in Example 2 to prepare Compound Nos. 10–16 listed in Table 3. Physicochemical data of these compounds are given in Table 4.

TABLE 3

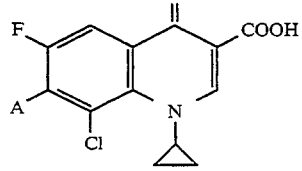

| Compound No. | A | Compound No. | A |
|---|---|---|---|
| 10 | CH₃-N(C=O)-CH₂CH₂-N— | 14 | HN-piperazinyl with NH₂ |
| 11 | hexahydroazepinyl with NH₂ | 15 | (R)-hexahydroazepinyl with NH₂ |
| 12 | hexahydroazepinyl | 16 | (S)-hexahydroazepinyl with NH₂ |
| 13 | hexahydroazepinyl with N(CH₃)₂ | | |

TABLE 4

| Compound No. | Melting Point(°C.) | Property | IR (KBr, cm$^{-1}$) | $^1$H-NMR ($\delta$ ppm) |
|---|---|---|---|---|
| 10 | 136–140 | light yellow powder | 1720, 1640, 1610 | 0.80–1.50(m, 4H), 2.80–3.00(m, 2H), 3.08(s, 3H), 3.30–3.80(m, 6H), 4.20–4.50(m, 1H), 8.15(d, J=11.6Hz, 1H), 9.00(s, 1H), (CDCl₃). |

TABLE 4-continued

| Compound No. | Melting Point(°C.), | Property | IR (KBr, cm$^{-1}$) | $^1$H-NMR (δ ppm) |
|---|---|---|---|---|
| 11 | 275–278 (decomposed) | colorless powder | 1610–1640 | 0.55–2.30(m, 4H), 1.40–1.95(m, 6H), 2.75–3.45(m, 5H), 4.00–4.30(m, 1H), 7.90 (d), J=11.6Hz, 1H), 8.75(s, 1H). (NaOD+D$_2$O). |
| 12 | 163–165 | light yellow powder | 1720, 1620 | 0.80–1.50(m, 4H), 1.55–2.00(m, 8H), 3.20–3.70(m, 4H), 4.24–4.55(m, 1H), 8.05(d, J=11.6Hz, 1H), 8.96(s, 1M). (CDCl$_3$). |
| 13 | 210–215 (decomposed) | light yellow powder | 1720, 1610 | 1.00–1.45(m, 4H), 1.60–2.20(m, 6H), 2.60–2.80(m, 6H), 3.00–3.60(m, 4H), 3.80–4.00(m, 1H), 4.15–4.30(m, 1H), 8.15(d, J=7.7Hz, 1H), 8.98(s, 1H). (CDCl$_3$). |
| 14 | 202–208 (decomposed) | brown powder | 1723, 1630 | 0.90–1.30(m, 4H), 2.60–4.20(m, 13H), 4.20–4.50(m, 1H), 7.93(d, J=11.0Hz, 1H), 8.81(s, 1H). (DMSO-d$_6$). |
| 15 | 255–257 (decomposed) | colorless powder | 1600–1640 | 0.50–1.30(m, 4H), 1.40–2.00(m, 6H), 2.75–3.50(m, 5H), 4.00–4.30(m, 1H), 7.90(d, J=11.6Hz, 1H), 8.65(s, 1H), (NaOD+D$_2$0). |
| 16 | 241–244 (decomposed) | colorless powder | 1600–1640 | 0.50–1.30(m, 4H), 1.40–2.00(m, 6H), 2.80–3.50(m, 5H), 4.10–4.40(m, 1H), 7.90(d, J=11.6Hz, 1H), 8.65(s, 1H), (NaOD+D$_2$0). |

EXAMPLES 17–21

Reactions were carried out in the same manner as in Example 1 or 2 to prepare Compound Nos. 17–21 listed in Table 5. Physicochemical data of these compounds are given in Table 6.

TABLE 5

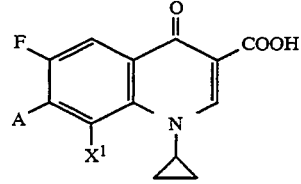

| Compound No. | A | X$^1$ | Compound No. | A | X$^1$ |
|---|---|---|---|---|---|
| 17 | | H | 20 | | Cl |
| 18 | | H | 21 | | Cl |
| 19 | 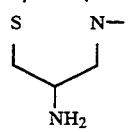 | H | | | |

TABLE 6

| Compound No. | Melting Point(°C.), | Property | IR (KBr, cm$^{-1}$) | $^1$H-NMR (δ ppm) |
|---|---|---|---|---|
| 17 | 231–233 | light yellow powder | 1720, 1625 | 1.10–1.40(m, 4H), 1.80–2.20(m, 2H), 2.50–2.70(m, 2H), 2.80–3.10(m, 2H), 3.60–4.00(m, 5H), 7.33(d, J=7.9Hz. 1H), 7.80(d, J=15.4Hz, 1HY), 8.58(s, 1H), (DMSO-d$_6$). |
| 18 | 238–239 | light brown powder | 1712, 1625 | 1.10–1.40(m, 4H), 1.8–2.2(m, 2H), 3.6–4.0(m, 9H), 7.38(d, J=8.1Hz, 1H), 7.81 (d. J=14.7Hz, 1H), 8.59(s, 1H). (DMSO-d$_6$). |
| 19 | | colorless plate crystals | | 0.60–1.20(m, 4H), 2.20–3.40(m, 9N), 7.10(d, J=8.0Hz, 1H), 7.60(d, J=15.0Hz, 1H), 8.50(s, 1H). (DMSO-d6). |
| 20 | | yellow powder | | 0.80–1.40(m, 4H), 1.80–2.20(m, 2H), 2.80–4.20(m, 10H; 1H disappeared with D$_2$0);8.09(d, J=10.8Hz, 1H), 8.93(s, 1H). (CDCl$_3$). |
| 21 | 181–183 | colorless needles | 1726, 1602 | 0.80–1.40(m, 4H), 1.60–1.90(br, 1H; disappeared with D$_2$0), 1.90–2.30(m, 2H), 3.40–3.70(m, 4H), 3.70–4.10(m, 4H), 4.20–4.50(m, 1H), 8.03(d, J=11.0Hz, 1H), 8.91(s, 1H). (CDCl$_3$). |

Test Example 1

Antimicrobial Activity

Antimicrobial activities against bacteria listed in Tables 7–9 were measured according to the MIC measurement method of The Japan Chemotherapeutic Association. Ofloxacin was used as a control. The results are shown in Tables 7–9.

Medium: Mueller Hinton Medium

Sample dilution: A 1,000 mcg/ml solution in 25% dimethylsulfoxide was prepared. A series of solutions with various concentrations (100 mcg to 0.006 mcg) were prepared by successively diluting the solution with sterilized water by a factor of ½.

Amount of inoculated bacteria: 10$^6$/ml

Cultivation conditions: 37° C., 48 hours
Determination: after 24 hours

TABLE 7

| Tested Bacteria | MIC (μg/ml) | | |
|---|---|---|---|
| | Compound Number 2 | Compound Number 15 | Ofloxacin |
| Gram-positive bacteria | | | |
| 1. Bacillus subtilis ATCC 6633 | 0.024 | 0.024 | 0.098 |
| 2. Staphylococcus aureus FDA 209P | 0.012 | 0.012 | 0.195 |
| 3. Staphylococcus aureus Terajima | 0.098 | 0.195 | 0.78 |
| 4. Staphylococcus aureus Smith | 0.012 | 0.024 | 0.39 |
| 5. Staphylococcus epidermidis ATCC 12228 | 0.049 | 0.049 | 0.78 |
| 6. Sarcina lutea ATCC 9341 | 0.195 | 0.098 | 3.12 |
| 7. Streptococcus faecalis IFO 12964 | 0.195 | 0.195 | 1.56 |
| 8. Micrococcus lysodeikticus IFO 3333 | 0.049 | 0.195 | 1.56 |

TABLE 8

| Tested Bacertia | MIC (μg/ml) | | |
|---|---|---|---|
| | Compound Number 2 | Compound Number 15 | Ofloxacin |
| Gram-negative bacteria | | | |
| 9. Escherichia coli O-1 | 0.195 | 0.098 | 0.098 |
| 10. Escherichia coli K-12 | 0.39 | 0.098 | 0.098 |
| 11. Salmonella typhi TD | 0.098 | 0.049 | 0.024 |
| 12. Shigella flexneri 2b | 0.003 | 0.006 | 0.012 |
| 13. Pseudomonas aeruginosa IFO 13736 | 6.25 | 1.56 | 1.56 |
| 14. Pseudomonas aeruginosa P2 | 12.5 | 1.56 | 0.78 |
| 15. Pseudomanas aeruginosa IFO 12582 | 6.25 | 0.78 | 3.12 |
| 16. Klebsiella pneumonias ATCC 10031 | 0.012 | 0.012 | 0.024 |
| 17. Klebsiella pneumonias IFO 13541 | 0.098 | 0.049 | 0.024 |
| 18. Proteus vulgaris OXK | 0.024 | 0.049 | 0.049 |
| 19. Proteus rettgeri | 0.78 | 0.195 | 0.098 |
| 20. Serratia marcescens NHL | 0.78 | 0.195 | 0.049 |

TABLE 9

| Tested Bacteria | MIC (μg/ml) | | |
|---|---|---|---|
| | Compound Number 2 | Compound Number 15 | Ofloxacin |
| Mesitylene-resistant streptococcus aureus gram-positive bacteria | | | |
| 21. M.R. Staphylococcus aureus 395 | 0.049 | 0.049 | 0.39 |
| 22. M.R. Staphylococcus aureus 415 | 0.024 | 0.024 | 0.39 |
| 23. M.R. Staphylococcus aureus 419 | 0.024 | 0.024 | 0.39 |
| 24. M.R. Staphylococcus aureus 420 | 0.024 | 0.049 | 0.39 |
| 25. M.R. Staphylococcus aureus 421 | 0.024 | 0.049 | 0.39 |

Industrial Applicability

The compound (1) and its salt of this invention exhibit a superior antimicrobial activity, especially against Gram positive microorganisms, and are thus useful for the treatments and prevention of various infectious diseases in clinics.

We claim:

1. A quinolone carboxylic acid derivative having the formula (I),

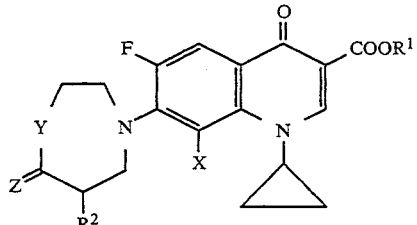

wherein Z is an oxygen atom, Y is N—$R^3$, wherein $R^3$ is a hydrogen atom or a lower alkyl group, $R^1$ is a hydrogen atom, an alkyl group, an aralkyl group, or an ester residual group which can be hydrolyzed in living bodies, $R^2$ is a hydrogen atom or an amino group which may be substituted by one or two lower alkyl groups and X is a hydrogen atom or a halogen atom; or a salt thereof.

2. The quinolone carboxylic acid derivative of claim 1, wherein Z is an oxygen atom, Y is NH, $R^1$ is a hydrogen atom, $R^2$ is hydrogen atom, and X is a hydrogen atom or a halogen atom; or a salt thereof.

3. The quinolone carboxylic acid derivative of claim 1, wherein X is a chlorine atom.

4. The quinolone carboxylic acid derivative of claim 2, wherein X is a chlorine atom.

5. The quinolone carboxylic acid derivative of claim 1, wherein $R^3$ is a hydrogen atom or a $C_1$-$C_5$-alkyl group.

6. The quinolone carboxylic acid derivative of claim 1, wherein $R^2$ is a hydrogen atom or an amino group which may be substituted by one or two $C_1$-$C_5$-alkyl groups.

7. The quinolone carboxylic acid derivative of claim 1, wherein $R^1$ is a hydrogen atom; a $C_1$-$C_{12}$-alkyl group; an aralkyl group selected from the group consisting of benzyl, phenylethyl, methylbenzyl, and naphthylmethyl; or an ester residual group which can be hydrolyzed in living bodies.

8. The quinolone carboxylic acid derivative of claim 1, wherein $R^3$ is a hydrogen atom or a $C_1$-$C_5$-alkyl group, $R^1$ is a hydrogen atom; a $C_1$-$C_{12}$-alkyl group; an aralkyl group selected from the group consisting of benzyl, phenylethyl, methylbenzyl, and naphthylmethyl; or an ester residual group which can be hydrolyzed in living bodies, and $R^2$ is a hydrogen atom or an amino group which may be substituted by one or two $C_1$-$C_5$-alkyl groups.

9. An antimicrobial composition, comprising an antimicrobially effective amount of a quinolone carboxylic acid derivative of formula (I)

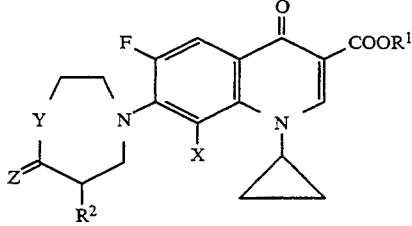

wherein Z is an oxygen atom, Y is N—$R^3$, wherein $R^3$ is a hydrogen atom or a lower alkyl group, $R^1$ is a hydrogen atom, an alkyl group, an aralkyl group, or an ester residual group which can be hydrolyzed in living bodies, $R^2$ is a hydrogen atom or an amino group which may be substituted by one or two lower alkyl groups and X is a hydrogen atom or a halogen atom; or a salt thereof, and a pharmaceutically acceptable carrier.

10. The composition of claim 9, wherein Z is an oxygen atom, Y is NH, $R^1$ is a hydrogen atom, $R^2$ is a hydrogen atom, and X is a hydrogen atom or a halogen atom; or a salt thereof.

11. The composition of claim 9, wherein X is a chlorine atom.

12. The composition of claim 10, wherein X is a chlorine atom.

13. The composition of claim 9, wherein $R^3$ is a hydrogen atom or a $C_1$–$C_5$-alkyl group.

14. The composition of claim 9, wherein $R^2$ is a hydrogen atom or an amino group which may be substituted by one or two $C_1$–$C_5$-alkyl groups.

15. The composition of claim 9, wherein $R^1$ is a hydrogen atom; a $C_1$–$C_{12}$-alkyl group; an aralkyl group selected from the group consisting of benzyl, phenylethyl, methylbenzyl, and naphthylmethyl; or an ester residual group which can be hydrolyzed in living bodies.

16. The composition of claim 9, wherein $R^3$ is a hydrogen atom or a $C_1$–$C_5$-alkyl group, $R^1$ is a hydrogen atom; a $C_1$–$C_{12}$-alkyl group; an aralkyl group selected from the group consisting of benzyl, phenylethyl, methylbenzyl, and naphthylmethyl; or an ester residual group which can be hydrolyzed in living bodies, and $R^2$ is a hydrogen atom or an amino group which may be substituted by one or two $C_1$–$C_5$-alkyl groups.

17. A method for curing an infectious disease caused by a microorganism, comprising administering to a patient in need thereof an effective amount of a quinolone carboxylic acid derivative of the formula (I)

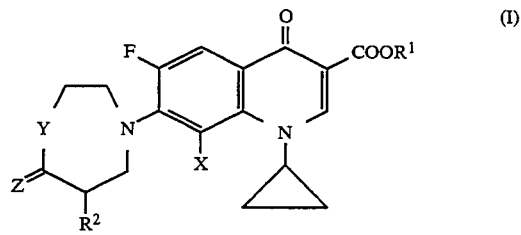

wherein Z is an oxygen atom, Y is N—$R^3$, wherein $R^3$ is a hydrogen atom or a lower alkyl group, $R^1$ is a hydrogen atom, an alkyl group, an aralkyl group, or an ester residual group which can be hydrolyzed in living bodies, $R^2$ is a hydrogen atom or an amino group which may be substituted by one or two lower alkyl groups and X is a hydrogen atom or a halogen atom; or a salt thereof.

18. The method of claim 17, wherein Z is an oxygen atom, Y is NH, $R^1$ is a hydrogen atom, $R^2$ is a hydrogen atom, and X is a hydrogen atom or a halogen atom; or a salt thereof.

19. The method of claim 17, wherein X is a chlorine atom.

20. The method of claim 18, wherein X is a chlorine atom.

21. The method of claim 17, wherein $R^3$ is a hydrogen atom or a $C_1$–$C_5$-alkyl group.

22. The method of claim 17, wherein $R^2$ is a hydrogen atom or an amino group which may be substituted by one or two $C_1$–$C_5$-alkyl groups.

23. The method of claim 17, wherein $R^1$ is a hydrogen atom; a $C_1$–$C_{12}$-alkyl group; an aralkyl group selected from the group consisting of benzyl, phenylethyl, methylbenzyl, and naphthylmethyl; or an ester residual group which can be hydrolyzed in living bodies.

24. The method of claim 17, wherein $R^3$ is a hydrogen atom or a $C_1$–$C_5$-alkyl group, $R^1$ is a hydrogen atom; a $C_1$–$C_{12}$-alkyl group; an aralkyl group selected from the group consisting of benzyl, phenylethyl, methylbenzyl, and naphthylmethyl; or an ester residual group which can be hydrolyzed in living bodies, and $R^2$ is a hydrogen atom or an amino group which may be substituted by one or two $C_1$–$C_5$-alkyl groups.

* * * * *

UNITED STATES PATENT AND TRADEMARK OFFICE
CERTIFICATE OF CORRECTION

PATENT NO.   : 5,385,900
DATED        : January 31, 1995
INVENTOR(S)  : Fujiko KONNO, et al.

It is certified that error appears in the above-indentified patent and that said Letters Patent is hereby corrected as shown below:

On the title page, Item [54], and Column 1, Line 1, the title should read:

--QUINOLONE CARBOXYLIC ACID DERIVATIVES--

Signed and Sealed this

Twenty-fifth Day of April, 1995

Attest:

BRUCE LEHMAN

*Attesting Officer*        *Commissioner of Patents and Trademarks*